US006699845B2

United States Patent
Oobae et al.

(10) Patent No.: US 6,699,845 B2
(45) Date of Patent: Mar. 2, 2004

(54) EXCIPIENT

(75) Inventors: Kazuhiro Oobae, Nobeoka (JP); Etsuo Kamada, Nobeoka (JP); Shun'ichi Gomi, Nobeoka (JP)

(73) Assignee: Asahi Kasei Kabushiki Kaisha (JP)

( * ) Notice: Subject to any disclaimer, the term of this patent is extended or adjusted under 35 U.S.C. 154(b) by 0 days.

(21) Appl. No.: 09/759,104

(22) Filed: Jan. 12, 2001

(65) Prior Publication Data

US 2002/0042393 A1 Apr. 11, 2002

Related U.S. Application Data

(63) Continuation of application No. PCT/JP99/03775, filed on Jul. 13, 1999.

(30) Foreign Application Priority Data

Jul. 15, 1998 (JP) ............................. 10-200295
Nov. 13, 1998 (JP) ............................. 10-323560

(51) Int. Cl.$^7$ ................ A61K 31/7016; A61K 31/715; A61K 9/14; C07H 3/04
(52) U.S. Cl. ................. 514/53; 514/777; 536/123.1; 536/124; 536/4.1; 424/489
(58) Field of Search .................. 514/777, 53; 536/4.1, 536/123.1, 124; 424/489

(56) References Cited

U.S. PATENT DOCUMENTS

| 4,678,812 A | 7/1987 | Bollin et al. |
| 4,762,857 A | 8/1988 | Bollin et al. |
| 5,591,612 A | * 1/1997 | Maruta et al. |

FOREIGN PATENT DOCUMENTS

| EP | 0 690 130 A1 | 1/1996 |
| JP | A-05-271054 | 10/1993 |
| JP | A-06-009382 | 1/1994 |
| JP | A-06-217716 | 8/1994 |
| JP | A-07-143876 | 6/1995 |
| JP | A-08-104650 | 4/1996 |
| JP | A-08-291051 | 11/1996 |
| JP | A-08-333243 | 12/1996 |
| JP | A-09-009986 | 1/1997 |
| JP | A-09-048726 | 2/1997 |
| JP | A-09-154493 | 6/1997 |
| JP | A-09-316006 | 12/1997 |
| JP | A-11-116464 | 4/1999 |
| WO | WO93/15724 | 8/1993 |
| WO | WO95/20380 | 8/1995 |
| WO | WO97/09037 | 3/1997 |
| WO | WO 97/28788 | 8/1997 |
| WO | WO97/47287 | 12/1997 |
| WO | WO98/05305 | 2/1998 |

OTHER PUBLICATIONS (Sigma Chemical Company Catalog (Biochemicals Organic Compounds for Research and Diagnostic Reagents), 1994 edition.*
Minoru Okada, Yasuo Ikeda, Jenji Ono, Toshiaki Kurazumi, Syuichi Kasai and Katsumi Imamori, "Quickly Soluble Solid Preparations", Database CA Online!, Chemical Abstracts Service, Columbus, Ohio, U.S., Database accession No. 130:272038 XP002186750, abstract, 2 pages.

* cited by examiner

*Primary Examiner*—Samual Barts
*Assistant Examiner*—Michael C. Henry
(74) *Attorney, Agent, or Firm*—Dickstein, Shapiro, Morin & Oshinsky, LLP.

(57) ABSTRACT

An excipient comprising trehalose having a purity of 99.0% or more, a proportion of particles of 75 $\mu$m or more of 2 to 90 wt %, an average particle size of 10 to 250 $\mu$m, an apparent specific volume of 1.5 to 3.5 ml/g, and a whiteness of 90% or more.

10 Claims, No Drawings

EXCIPIENT

This is a continuation of application no. PCT/JP99/03775, filed Jul. 13, 1999.

TECHNICAL FIELD

The present invention relates to an excipient useful for preparing tablets, capsules, powders, fine granules, granules and the like which are used as medicine, food, etc., and a pharmaceutical composition containing said excipient. More particularly, the present invention relates to an excipient comprising specific trehalose and a pharmaceutical composition containing said excipient.

BACKGROUND ART

An excipient used for formulating a drug into a pharmaceutical composition is desired to have a low reactivity with the drug and impart fluidity, compactibility and disintegrating properties of powder, with good balance among them, for the preparation of tablets by direct compressing. In order to, for example, prepare a pharmaceutical composition such as a powder, fine granules or granules by mixing the components of the pharmaceutical composition and then subjecting the resulting mixture to a processing treatment such as granulation by the use of a suitable wetting material, and, if necessary, prepare wet tablets by compressing the granules, the excipient is desired to have, for example, the following characteristics at the same time: the excipient has a good miscibility at the time of mixing powders, from the viewpoint of uniformity of the content of a drug, the excipient has a proper affinity for the wetting material and has such good granulating properties that its particles can be aggregated by the binding force of the particles, and the excipient improves the compactibility of granules and can impart sufficient disintegrating properties. In addition, since the excipient generally occupies the major portion of a pharmaceuitcal composition, it is desired to be inexpensive from the viewpoint of the cost of preparation of the pharmaceutical composition.

For thus imparting desirable physical properties to a pharmaceutical composition, the excipient is required to have various functions at the same time. In such an excipient, generally lactose are used among sugars, mannitol among sugar alcohols, and starch among natural polysaccharides. Lactose, however, is disadvantageous in that when a drug having an amino group is formulated into a pharmaceutical composition, lactose reacts with the drug and hence is difficult to be used for formulating such a drug into a pharmaceutical composition. In addition, since lactose has a low solubility in a wetting material, it has a very weak ability to aggregate the particles and hence is poor in granulating properties. Moreover, when a pharmaceutical composition having practical tablet hardness is prepared by using lactose, the pharmaceutical composition is very poor in disintegrating properties, so that the addition of a disintegrating agent has been necessary. Mannitol has no reducing properties and has a low reactivity with drugs, but it has been disadvantageous in that it strongly adheres to a die and a punch during compression into tablets and that since mannitol is poor in compactibility, a high compression pressure is required for attaining a sufficient tablet hardness to withstand impact during transportation and resulting in accelerated consumption of the die and the punch. Furthermore, mannitol has been disadvantageous in that because of its insufficient solubility in a wetting material, mannitol has a weak ability to aggregate the particles and hence is poor in granulating properties. Starch imparts disintegrating properties but has been disadvantageous in its low fluidity. Moreover, although starch has a disintegrating function, starch has been disadvantageous not only in that it cannot be formulated into a pharmaceutical composition without adding a binder because starch has almost no compactibility, but also in that it cannot be formulated into a pharmaceutical composition without adding a granulation adjuvant because starch has insufficient granulating properties.

As described above, the excipients among sugars and sugar alcohols which are used for formulating a drug into a pharmaceutical composition have both advantages and drawbacks, and a means for attaining desirable characteristics of the pharmaceutical composition, such as combination of the excipients is necessary. Therefore, much time and labor are required for the formulation and hence an excipient having a good balance among low reactivity, fluidity, miscibility, compactibility, granulating properties and the like is desired.

Trehalose is a nonreducing disaccharide and there are many reports that trehalose is not reactive with drugs. Known trehalose preparations, however, are expensive for reasons such as a high material cost, a low purity and a low yield in their production, and a mode for using them as an excipient which includes, for example, using them in a large amount in the formulation of a drug into a pharmaceutical composition has been not practical. In addition, no information has been obtained about the most suitable physical properties for imparting low reactivity, fluidity, miscibility, compactibility, granulating properties and the like to trehalose with good balance among them when trehalose is used as an excipient.

As to employment of trehalose as an excipient, International Publication No. WO 98/5305 discloses tablets of clavulanic acid and amoxycillin containing trehalose and other excipients. The specification of this reference describes the trehalose as a crystalline hydrate, a glassy amorphous substance or an anhydride (an anhydrous amorphous trehalose or an anhydrous crystalline trehalose) and describes the anhydrous amorphous trehalose as preferable from the viewpoint of drug stabilization and moisture barrier effect. The specification describes the particle size of the anhydrous amorphous trehalose or the crystalline hydrate as 50 to 500 $\mu$m, preferably 100 to 250 $\mu$m, from the viewpoint of fluidity. International Publication No. WO 97/9037 discloses effervescent tablets obtained by low-pressure compression which contain an excipient selected from trehalose, maltitol, sorbitol and the like. As to characteristics of the excipient, this reference describes the average particle size of the excipient as preferably about 100 to about 125 $\mu$m. These references, however, do not describe the proportion of particles of 75 $\mu$m or more and the apparent specific volume of the excipient, and even excipients having an average particle size within the ranges described in the references are not sufficient in fluidity and miscibility in some cases. For example, even powders of excipients having an average particle size within the ranges described in the references are poor in fluidity and are, for example, consolidated to fall in a had state of preservation when the proportion of fine particles in the powder is high. In addition, when the proportion of coarse particles in the powder is high, the powder is poor in miscibility with other components of a pharmaceutical composition. When the miscibility is bad, the pharmaceutical composition lacks uniformity of the content of a drug. The above reference do not describe granulating properties, compactibility and disintegrating properties and have given no consideration to the stability of a drug as well as physical properties of trehalose having a good balance among fluidity, miscibility, granulating properties, compactibility, disintegrating properties and the like. JP-A-6-217716 discloses an additive for preparing a pharmaceutical composition which comprises trehalose. The trehalose described therein, however, has a melting point of 203° C. and is an anhydride (according to the item "trehalose" in "Rikagaku-Jiten, 4th ed." IWANAMI-SHOTEN Ltd. (1987), the melting point of trehalose anhydride is 203° C. and the melting point of trehalose dihydrate is 97° C.). The anhydride is not desirable because it absorbs moisture with the lapse of time which changes physical properties of a pharmaceutical composition. This prior art reference describes trehalose capable of completely passing a 200-mesh screen as preferable, but such trehalose has been disadvantageous in its low fluidity. This prior art reference does not describe the proportion of particles of 75 $\mu$m or more, average particle size and apparent specific volume of trehalose, and has given no consideration to the stabilization of a drug as well as physical properties of trehalose having a good balance among fluidity, miscibility, granulating properties, compactibility, disintegrating properties and the like.

JP-A-7-143876 and JP-A-9-9986 disclose production processes of trehalose comprising treating one or more starch degradation products with enzymes, and compositions as foods, cosmetics or medicines which contain said trehalose. The production processes disclosed in these references permit production of trehalose at low cost because the material cost is low in the production processes. However, trehalose produced by any of the processes disclosed in the references has a purity of only about 95% and contains a large amount of glucose as an impurity in some cases. It has not been known at all that such an impurity deteriorates the stability of a drug in some cases. Moreover, trehalose produced by any of the processes disclosed in the references is in the form of coarse crystals and cannot impart fluidity, miscibility, granulating properties, compactibility, disintegrating properties and the like with good balance among them when used as it is, but this fact has not been considered at all.

The specifications of U.S. Pat. Nos. 4,678,812 and 4,762,857 disclose powders prepared by S-1 spray process which contain trehalose. In the S-1 spray process, all components to be formulated into tablets are mixed, suspended or dissolved in a solvent and then subjected to spray drying, in order to improve the content uniformity. JP-A-9-154493 discloses a trehalose-containing syrup. When used in the mode described in any of these references, trehalose is not always required to have characteristics required of an excipient in compression into tablets, granulation or the like, such as fluidity, compactibility, disintegrating properties, granulating properties and the like of powder. The importance of and necessity for physical properties required of specific trehalose in compression into tablets, granulation or the like have not been considered in the above references. When a drug, an excipient and the like are mixed each in the form of powder and the mixed powder is divided and then suspended or dissolved in a solvent or the like, properties of powder of the trehalose according to the present invention are desirable because they ikpart an excellent content uniformity. The above references do not disclose this fact.

Many patent proposals have been made for utilization of sugars as excipients for preparing a pharmaceutical composition, in particular, their utilization in molded products which disintegrate rapidly in mouth.

JP-A-5-271054 discloses intraoral dissolution type tablets obtained by compressing a mixture of an active ingredient, a sugar and water contained in such a volume that the surfaces of particles of said sugar are wetted, and a process for producing the tablets. In this reference, sugars (e.g. white sugar and coupling sugar), starch sugars (e.g. glucose, maltose and maltose syrup powder), lactose, honey, sugar alcohols (e.g. sorbitol and mannitol), etc. are mentioned as the sugar.

International Publication No. WO 93/15724 discloses rapidly-soluble tablets comprising a sugar or a sugar alcohol as a main constituent which is obtained by subjecting a kneaded product to compression molding before drying in the production of the tablets by a wet granulation method. In this reference, white sugar, lactose, glucose, fructose, xylitol, sorbitol and mannitol are mentioned as the sugar or sugar alcohol.

JP-A-9-48726 discloses an intraoral rapidly-disintegrable pharmaceutical composition obtained by mixing a sugar, a sugar alcohol, a water-soluble high-molecular weight substance and a drug; moistening and wetting the mixture at a low density; and then drying the mixture. In this reference, glucose, fructose, white sugar, mannitol and sorbitol are mentioned as the sugar and the sugar alcohol.

International Publication No. WO 97/47287 discloses tablets comprising a sugar alcohol or sugar having an average particle size of 30 $\mu$m or less, an active ingredient and a disintegrating agent. In this reference, D-mannitol, sorbitol, lactose and glucose are mentioned as the sugar alcohol or sugar.

Internation Publication No. WO-95/20380 discloses an intraoral dissolution type compression-molded product that comprises a sugar having a low compactibility and a sugar having a high compactibility and is rapidly disintegrated and dissolved in mouth, and a process for producing said molded product. In this reference, lactose, mannitol, glucose, white sugar and xylitol are mentioned as the former sugar, and maltose, maltitol, sorbitol and oligosaccharides are mentioned as the latter sugar.

As other publications concerning molded products that are rapidly disintegrated or dissolved in mouth, there are JP-A-8-333243, JP-A-9-316006, Japanese Patent No. 2540131, JP-A-8-291051, etc. But, these publications do not describe employing trehalose at all. Moreover, the balance between the hardness and intraoral disintegrating properties of the molded product is not sufficient in some cases. That is, when the molded product is rapidly disintegrated, its hardness is not sufficient in some cases. On the other hand, when the compression pressure is increased in order to impart a sufficient hardness to the molded product, the disintegration of the molded product is retarded in some cases. Furthermore, generally used lactose and sugar alcohols have been disadvantageous in that they exhibit laxative effect in some cases.

Page 166 of "Collection of the summaries of lectures in the 15th symposium on particulate preparations and designs (1998)" describes a case where trehalose is used as a sugar, but it does not describe physical properties of trehalose at all. In this reference, employment of trehalose in intraoral disintegrable tablets was investigated in practice, but the disintegration of a molded product obtained by using trehalose was not sufficient though its hardness was somewhat high. Thus, the molded product gave an unsatisfactory result as a rapidly disintegrable molded product.

JP-A-11-116464 describes employment of trehalose in a rapidly soluble solid pharmaceutical composition that is rapidly disintegrated and dissolved in mouth, but it does not describe physical properties of trehalose required for imparting compactibility, disintegrating properties and the like with good balance among them.

DISCLOSURE OF THE INVENTION

The present invention is intended to provide an excipient comprising trehalose which has a low reactivity with drugs and can impart various physical properties required for preparing a pharmaceutical cokposition, such as fluidity, miscibility (the uniformity of the content of a drug), compactibility, disintegrating properties, granulating properties and the like with good balance among them. The present invention is also intended to provide a pharmaceutical composition that has a low reactivity and is good in various properties such as fluidity, compactibility, disintegrating properties, granulating properties and the like. The present invention is further intended to provide a rapidly disintegrable molded product such as tablets used as a medicine, food or the like, which is rapidly disintegrated and dissolved immediately after being put in mouth or water, and has a sufficient hardness to be free from damage during its production, transportation or storage, and a process for producing said molded product.

The present inventors earnestly investigated and consequently found that employment of trehalose with specific physical properties as an excipient solves the problems described above, whereby the present invention has been accomplished.

That is, the present invention relates to (1) an excipient comprising trehalose having a purity of 99.0% or more, a proportion of particles of 75 μm or more of 2 to 90wt %, an average particle size of 10 to 250 μm, an apparent specific volume of 1.5 to 3.5 ml/g, and a whiteness of 90% or more;

(2) an excipient according to the above item (1), wherein the content of glucose as an impurity in said trehalose is less than 1.0%;

(3) an excipient according to the above item (1), wqherein the purity of the trehalose is 99.3% or more, the content of glucose as an impurity in the trehalose is 0.5% or less, and the average particle size of the trehalose is 10 to 150 μm;

(4) an excipient according to the above item (3), which has an average particle size of 30 to 150 μm;

(5) an excipient according to the above item (1), wherein the trehalose is a dihydrate;

(6) an excipient according to the above item (1), wherein the trehalose is that obtained by treating one or more starch degradation products having a degree of glucose polymerization of 3 or more, with enzymes;

(7) an excipient according to the above item (1), which is for processing and formulating a solid into a pharmaceutical composition;

(8) a pharmaceutical composition comprising an excipient according to any one of the above itesm (1) to (7);

(9) a pharmaceutical cokposition according to the above item (8), which is a rapidly disintegrable molded product;

(10) a pharmaceutical composition according to the above item (9), which further comprises a cellulose;

(11) a process for producing an excipient according to the above item (1, which comprises processing trehalose crystals by at least one treating method selected from the group consisting of purification, grinding, sieving and crystallization;

(12) a production process according to the above item (11, wherein the trehalose crystals are those obtained by treating one or more starch degradation products having a degree of glucose polymerization of 3 or more, with enzymes;

(13) a production process according to the above item (11), wherein the content of glucose as an impurity in the trehalose is less than 1.0%; and

(14) a production process according to any one of the above items (11) to (13), wherein said treating method comprises grinding under conditions under which the amount of impact energy is small.

BEST MODE FOR CARRYING OUT THE INVENTION

As the trehalose used in the present invention, α,α-trehalose, α,β-trehalose or β, β-trehalose can be used, though α,α-trehalose which exists in nature is preferable. In a solid state, trehalose exists in either of two forms, namely, it exists in the form of anhydride or dihydrate. The dihydrate is preferable because it does not absorb moisture with the lapse of time. In particular, the dihydrate in a crystalline state is preferable. The dihydrate can be distinguished by the appearance of a peak of heat of fusion near 100° C. in DSC measurement.

The trehalose referred to herein is that obtained by treating one or more starch degradation products having a degree of glucose polymerization of 3 or more, with enzymes. From the viewpoint of cost, it is preferable for industrial utilization to use trehalose obtained by purification, grinding, particle size adjustment and the like of the following starting material: for example, commercial trehalose ("Trehaose" available from Hayashibara Biochemical Laboratories, Inc.) or the trehalose disclosed in JP-A-7-143876 and produced from one or more starch degradation products, for example, by a process using enzymes (a trehalose preparation having an increased trehalose content which is obtained by treating a solution containing one or more reducing starch partial-degradation products selected from those having a degree of glucose polymerization of 3 or more, with an enzyme capable of producing nonreducing sugars having a trehalose structure at the end from the one or more reducing starch partial-degradation products selected from those having a degree of glucose polymerization of 3 or more, and then with glucoamylase or α-glucosidase to obtain a solution containing trehalose and sugars as contaminants, and subjecting this solution to a column chromatography using a strongly acidic cation-exchange resin.

The purity of the trehalose is 99.0% or more. The content of glucose as impurity in the trehalose is preferably less than 1.0%. When the purity of the trehalose is less than 99.0% or its glucose content is 1.0% or more, the trehalose tends to be increased in reactivity with an active ingredient. High-purity trehalose is expected to function as a stabilizer for a drug, but it has not been known that the presence of a slight amount of glucose as impurity markedly deteriorates the stability of a drug. The purity of the trehalose is preferably 99.3% or more. The glucose content is preferably 0.5% or less, in particular, 0.3% or less. Although the purity of the trehalose and the glucose content are preferably brought close to 100% and 0%, respectively, as much as possible, trehalose may be purified in view of labor required for the purification and the effect of the purification because the purification decreases the yield and raises the cost.

The average particle size of the trehalose is 10 to 250 μm. When the average particle size is less than 10 μm, the fluidity and the handleability are deteriorated because the aggregating properties of powder of the trehalose are enhanced. Moreover, the disintegrating properties of a molded product are deteriorated probably because the void content of the molded product is decreased. When the average particle size is more than 250 μm, the miscibility with an active ingredient and other additives is deteriorated, so that the content of each of the active ingredient and the like in a pharmaceutical composition obtained by the use of the trehalose is not uniform. Furthermore, particles of the trehalose are coarse and hence feel rough in mouth at first. The average particle size of the trehalose is preferably 20 to 150 μm, most preferably 30 to 100 μm.

As to the particle size of powder of the trehalose, the proportion of particles having a particle size of 75 μm or more is preferably 2 to 90 wt %. When the proportion is less than 2 wt %, the fluidity of the powder is remarkably deteriorated. When the proportion is more than 90 wt %, the miscibility with an active ingredient and the like is deteriorated, so that the content of each of the active ingredient and the like in a pharmaceutical composition obtained by the use of the trehalose is not uniform. The proportion of particles having a particle size of 75 μm or more is preferably, in particular, 5 to 80 wt %, more preferably 10 to 60 wt %.

The apparent specific volume of the trehalose is 1.5 to 3.5 ml/g. When the apparent specific volume is less than 1.5 ml/g, the miscibility with an active ingredient and other additives is deteriorated, so that the content of each of the active ingredient and the like in a pharmaceutical composition obtained by the use of the trehalose is not uniform. When the apparent specific volume is more than 3.5 ml/g, the fluidity of powder of the trehalose is remarkably deteriorated, resulting in a low handleability. Therefore, such an apparent specific volume is not practical. The apparent specific volume of the trehalose is preferably 1.5 to 3.0 ml/g, in particular, 1.6 to 2.5 ml/g.

By thus controlling the physical properties of the trehalose so that they may be within the specific ranges specified in the present invention, various physical properties required for preparing a pharmaceutical composition can be imparted with good balance between them, and the pharmaceutical composition can be prepared without using other excipients together with the trehalose.

In addition, the whiteness of the trehalose is 90% or more, preferably 93% or more. The rating for the quality of a pharmaceutical composition often goes up with an increase in the external whiteness of the pharmaceutical composition. When a pharmaceutical composition is colored, its color desirably becomes clearer with an increase in the whiteness of an additive. Therefore, when the whiteness of the trehalose is less than 90%, the trehalose cannot be used in practice.

The trehalose used in the present invention can be obtained by subjecting, for example, commercial trehalose crystals or trehalose crystals obtained by treating one or more starch degradation products having a degree of glucose polymerization of 3 or more with enzymes, to a proper combination of processing steps selected from purification, grinding, sieving, crystallization and the like. A method for the trehalose purification is not particularly limited so long as it is a method of removing glucose, such as passage through an ion-exchange resin, adjustment of the number of column fractionating operations for sugars contained in a stock solution, recrystallization, conversion of glucose to a sugar alcohol by hydrogenation, or the like. The grinding is conducted with a dry-grinding mill such as a roller mill, hammer mill, pin mill, ball mill, vibration mill, jet mill, vibration ball mill or the like. The sieving may be conducted by using a continuous vibration screen, a pneumatic conveying screen or the like. Although the types of the grinding mill and the screen are not particularly limited so long as the proportion of particles of 75 μm or more, average particle size and apparent specific volume of the treated trehalose are within the ranges specified in the present invention, the grinding is preferably conducted by setting impact energy during the grinding at a low value because the physical property values specified in the present invention enable the trehalose to exhibit functions (e.g. fluidity, miscibility, granulating properties, hygroscopicity, compactibility and disintegrating properties) as an excipient with good balance between them and keep a product in a good state of preservation (for example, they prevent consolidation). Trehalose is easily ground because it is crystalline powder. When trehalose is excessively ground, its fine particles bind strongly to one another, so that there is a fear of consolidation. It is conjectured that this phenomenon is caused by the strong binding power of trehalose particles for one another.

When the consolidation occurs, advantageous powder characteristics are undesirably lost. The particle size of the particles obtained by grinding is expressed as a function of impact energy applied to the particles. The whole energy produced by the grinding mill is not applied to particles but is partially lost as heat. The degree of the loss varies depending on the type and kind of the grinding mill, and the energy produced by the grinding mill should be controlled in order that particles obtained by the grinding may have the above-mentioned desirable physical properties. The feed rate capable of determining the amount of powder in the grinding chamber of the grinding mill is also a factor that changes the amount of the impact energy. For example, when the feed rate is high, the number of collisions with a grinding blade is small, so that the amount of impact energy applied to particles is small. In addition, when particles are discharged from the grinding chamber of the grinding mill, the opening of a screen affects the residence time of powder in the grinding chamber. When the screen opening is large, the residence time of particles in the grinding chamber is short. When the screen opening is small, the residence time is long. Therefore, the screen opening is also a factor that affects the impact energy. From these facts, it can be seen that the impact energy is energy applied to particles in practice. For example, in the case of a hammber mill, the energy produced, feed rate, screen opening and the like in the grinding mill determine the amount of the impact energy. For example, when a hammer mill is used, the amount of energy produced is adjusted to 20 to 90% and the feed rate and the screen opening are properly determined. In the case of, for example, a bantam mill, the number of revolutions is controlled in a range of 3,000 to 15,000 rpm and the feed rate is controlled in a range of 3 to 6 kg/hr though depending on the particle size of a starting material. When the number of revolution is above the range described above, adhesion and aggregation during storage tend to occur. When the number of revolutions is below the range described above, the proportion of coarse particles is increased. The screen opening is properly varied depending on the degree of grinding and is set in a range of 0.3 mmφ to maximum (no screen). When the residence of particles in the grinding mill is taken into consideration, the screen opening is preferably 0.5 to 3.0 mmφ. In the case of a jet mill, since excessive grinding tends to take place because a large amount of impact energy is applied during grinding, the air pressure is preferably adjusted to 3.5 kg/cm$^2$ or less.

The trehalose used in the present invention and having the properties described above exhibits various functions as an excipient with good balance among them, and is especially useful as an excipient for processing and formulating powder into a pharmaceutical composition.

Although the excipient referred to herein may be used in a pharmaceutical composition prepared in any final form such as a liquid, suspension, solid, paste of the like, it is preferably used in, in particular, a pharmaceutical composition prepared in a solid form, i.e., tablets, granules, powder or the like.

The pharmaceutical composition referred herein may contain pharmaceutically active ingredient powders, agrochemically active ingredient powders, active ingredient powders for fertilizer, active ingredient powders for feed, active ingredient powders for food, active ingredient powders for cosmetic, coloring matter powders, flavoring material powders, metal powders, ceramic powders, catalyst powders, surfactant powders, etc. besides the excipient of the present invention. In addition, the pharmaceutical composition may freely contain other excipients, disintegrating agents, binders, lubricants, sweeteners, etc. as additives if necessary.

The excipient for processing and formulating a solid into a pharmaceutical composition which is referred to herein is an excipient used for mixing an active ingredient and the excipient each in the form of powder and formulating the mixture into a pharmaceutical composition through a processing step such as granulation, compression into tablets, or the like without suspending or dissolving the mixture. As compositions containing the pharmaceutically active ingredient powder, there are mentioned extracts, tablets, powders, fine granules, granules, pills, capsules, troches, cataplasmas and the like, as well as compositions prepared at the time of use, among suspensions, solutions, syrups, liniments, lotions, etc.

Although the content of the excipient comprising trehalose of the present invention is varied depending on the content of an active ingredient, physical properties of a desired pharmaceutical composition, etc., it is preferably about 1 to about 99.9 wt % in a solid pharmaceutical composition such as tablets. When the content of the excipient is less than 1 wt %, desirable physical properties cannot be imparted to the pharmaceutical composition. When the content of the excipient is more than 99.9 wt %, the content of the active ingredient cannot be assured. The content of the excipient is preferably, in particular, about 5 to about 80 wt %, more preferably about 10 to about 70 wt %. For example, in a suspension-form or liquid pharmaceutical composition such as suspension, solution, syrup or the like, the excipient comprising trehalose of the present invention is preferably contained in a proportion of approximately 1 to 50 wt %. When the content is less than 1 wt %, desirable physical properties cannot be imparted to the pharmaceutical composition. When the content is more than 50 wt %, trehalose crystals are precipitated, so that characteristics required of the pharmaceutical composition cannot be attained. The content is preferably, in particular, about 5 to about 40 wt %, more preferably about 10 to about 30 wt %.

The rapidly disintegrable molded product referred to herein contains one or more active ingredients and optionally other additives in addition to the excipient comprising trehalose of the present invention. Although the content of the excipient comprising trehalose of the present invention is varied depending on the content of the active ingredient(s, physical properties of the desired molded product, etc., it is preferably about 5 to about 99.9 wt % in the molded product. When the content of the excipient is less than 5 wt %, the resulting molded product does not have hardness and disintegrating properties required of a rapidly disintegrable molded product. When the content of the excipient is more than 99.9 wt %, the content of the active ingredient(s) cannot be assured. The content of the excipient is preferably, in particular, about 10 to about 80 wt %, more preferably about 20 to about 70 wt %.

The active ingredient used in the present invention may be in any form such as powder, crystals, oil, solution or the like, and is used in molded products for oral administration, such as drugs for arrhythmia, hypotensors, vasodilators, diuretics, antipyretic analgesic antiphlogistics, antiulcer drugs, drugs for stomach and bowels, drugs for controlling intestinal function, therapeutic drugs for osteroporosis, antitussive expectorants, antasthmatics, antibacterials, drugs for pollakiurea, tonics, vitamin preparations, etc. As the active ingredient(s), an active ingredient or a combination of two or more active ingredients is used. The present invention includes not only pharmaceutical compositions but also compositions utilized in the form of a molded product, such as health foods, baths, drugs for animal, diagnostic drugs, agrochemicals, fertilizers, etc. The excipient of the present invention is especially effective for drugs having one or more amino groups because it is not reactive with the drugs.

Although the content of the active ingredients) is varied depending on the kind and characteristics of the active ingredient(s), it is approximately 0.01 to 90 wt % based on the weight of the molded product. When the content is less than 0.01 wt %, the active ingredient(s) is often ineffective. When the content is more than 90 wt %, the impartment of desirable rapidly disintegrating properties becomes difficult. The content is preferably 0.01 to 80 wt %, in particular, 0.01 to 50 wt %.

Other additives such as excipients, disintegrating agents, binders, lubricants, flavoring materials, coloring matters, sweeteners, surfactants, etc. may be freely added.

The excipients include, for example, celluloses such as microcrystalline cellulose, powdered cellulose, etc.; sugars such as white sugar, glucose, lactose, fructose, maltose, etc.; sugar alcohols such as mannitol, xylitol, maltitol, erythritol, sorbitol, etc.; starches such as corn starch, potato starch, etc.; and inorganic salts such as calcium hydrogenphosphate, calcium carbonate, silicic acid anhydride, hydrated silicic acid, aluminum silicate, calcium silicate, magnesium aluminate silicate, etc.

The disintegrating agents include, for example, celluloses such as sodium croscarmellose, calcium carmelose, carmelose, low-substituted hydroxypropyl cellulose, etc.; starches such as sodium carboxymethyl starch, hydroxypropyl starch, partly pregelatinized starch, etc.; and crospovidone.

The binders include, for example, celluloses such as hydroxypropyl cellulose, hydroxypropylmethyl cellulose, methyl cellulose, etc.; starches such as pregelatinized starch, starch paste, etc.; synthetic polymers such as poly(vinylpyrrolidone)s, carboxyvinyl polymers, etc.; and natural polymers such as sodium alginate, xanthan gum, gum arabic, etc.

The lubricants include magnesium stearate, calcium stearate, stearic acid, sucrose fatty acid esters, talc, etc.

The rapidly disintegrable molded product of the present invention can have an improved quality when produced by proper combination of not only one or more active ingredients and the excipient of the present invention but also the other excipients, the disintegrating agents, the binders, the lubricants and the like. There are preferably used, in particular, the celluloses, sugars, sugar alcohols and starches as the excipients; the celluloses as the disintegrating agents and the binders; the celluloses as the binders; and the stearates as the lubricants.

The molded product obtained by using the excipient comprising trehalose of the present invention is useful as a rapidly soluble molded product because it is rapidly disintegrated and dissolved immediately after being put in mouth or water and it has a proper hardness.

Usually, the disintegration time in mouth of the rapidly disintegrable molded product of the present invention and its disintegration time in the disintegration test prescribed in the Japanese Pharmacopoeia are preferably about 2 seconds to about 2.0 minutes. They are preferably, in particular, about 2 seconds to about 1.0 minute, more preferably about 3 seconds to about 30 seconds. Usually, the hardness of the molded product is preferably about 1 to about 20 kg. The hardness of the molded product is preferably, in particular, about 2 to about 12 kg, more preferably about 3 to about 8 kg.

The rapidly disintegrable molded product of the present invention can be produced according to a conventional process for producing a molded product. Several specific examples of production process are described below, but a process for producing the rapidly disintegrable molded product is not limited to the specific examples.

1. One or more active ingredients, the excipient of the present invention and optionally other additives are mixed and hen kneaded together with water, after which the kneaded mixture is compressed into tablets after being somewhat wetted depending on the presence of a drying step, and the tablets are dried. In this case, the compression pressure is usually about 3 to about 200 kg/cm$^2$, preferably about 5 to about 100 kg/cm$^2$, most preferably about 5 to about 50 kg/cm$^2$, though it is caried depending on the composition of the tablets.

2. A process according to the item 1, wherein a conventional wet tabletting method is adopted in which the kneaded mixture is compressed into tablets after being substantially dried.

3. One or more active ingredients, the excipient of the present invention and optionally other additives are mixed, placed in mold, and then allowed to stand under a load of about hundreds grams per square centimeter with heating and moistening.

4. A direct tabletting method is adopted in which one or more active ingredients, the excipient of the present invention and optionally other additives are mixed and then compressed into tablets as they are. The mixed powder may be compressed into tablets after being allowed to stand with moistening.

5. One or more active ingredients, the excipient of the present invention and optionally other additives are mixed and then kneaded together with water to obtain paste, which is placed in a mold and slowly dried as it is.

Molded products obtained by either of the processes 1 and 2 among the above processes are preferred because they have the best balance between the disintegrating properties and hardness of the molded product. When the rapidly disintegrable molded product of the present invention is incorporated with not only the excipient comprising trehalose but also other excipients, for example, celluloses including natural celluloses (e.g. microcrystalline cellulose and powdered cellulose) and cellulose derivatives (e.g.

low-substituted hydroxypropyl cellulose, methyl cellulose and sodium carboxymethyl cellulose), the compactibility are markedly improved, so that the compression pressure at molding into tablets step can be greatly reduced. Therefore, the incorporation is advantageous for attaining the rapidly disintegrating properties. The trehalose has good binding properties under a high compression pressure, so that its disintegration property tends to be retarded. When any of the celluloses is incorporated into the molded product, it acts as a disintegrating agent having an inhibitory effect on the retardation of the disintegration of the trehalose. When no cellulose is incorporated, a rapidly disintegrable molded product having a practical hardness (4 to 8 kg) and a disintegration time of 1 minute or less can be obtained by preparing tablets at a compression pressure of usually about 200 to about 1,000 kg/cm$^2$, though the compression pressure is varied depending on the composition of the molded product. When any of the celluloses is incorporated, a rapidly disintegrable compression-molded product having a practical hardness can be obtained at a compression pressure of approximately 100 to 500 kg/cm$^2$ without deteriorating the disintegrating properties. The reduction of the compression pressure is desirable for preventing adhesion to a die and a punch and improving the durability of the die and punch. The proportion of the cellulose incorporated is about 1 to about 30 wt %, preferably about 1 to about 20 wt %. When the proportion is less than 1 wt %, compactibility are not imparted even when the compression pressure is reduced. When the proportion is more than 30 wt %, an unpleasant taste, a rough feel and the like are given, so that the molded product gives an unpleasant feeling when taken.

The present invention is explained in further detail with the following examples.

In the examples, measurements are carried out as follows.
Trehalose Purity and Glucose Content Measured by the following method by converting the amounts of sugars, exclusive of their water of crystallization, to the amounts of their anhydrides.

(1) 1.0 Gram of a sample is accurately measured and then dissolved in water to obtain a solution having a total volume of accurately 100 ml.

(2) 20 Microliters of this solution is analyzed by liquid chromatography under the operating conditions described below.

(3) Peaks due to oligosaccharides, trehalose and glucose, respectively, appear in that order.

(4) Measurement is carried out by an automatic integration method, and the ratio of the peak area of trehalose or glucose to the total peak area is calculated.

Trehalose purity (%)=(A2/(A1+A2+A3))×100

Glucose content (%)=(A3/(A1+A2+A3))×100 wherein
A1: the peak area of oligosaccharides,
A2: the peak are of trehalose,
A3: the peak area of glucose.
Operating Conditions Detector: a differential refractometer (ERC-7515B)
Column: MCI-GEL CK04SS (Mitsubishi Chemical Industries Ltd.)
Column temperature: 85° C.
Mobile phase: water
Flow rate: 0.4 mL/min.

Water Content

Determined as a value obtained by measuring about 0.1 g of trehalose and determining its water content by the Karl Fisher method.

Proportion of Particles of 75 µm or More

Five grams of trehalose was weighed onto a screen having a screen opening of 75 µm, and sifted with Air Jet Sieve (Model 200LS, mfd. by ALPINE) for 5 minutes, and the weight percentage of the weight of particles remaining on the screen based on the total weight of particles was calculated as the proportion of particles of 75 µm or more.

Average Particle Size

Five grams of trehalose was sifted through screens having screen openings of 500 µm, 300 µm and 250 µm, respectively, and then sifted with Air Jet Sieve by using screens having screen openings of 150 µm, 75 µm, 45 µm, 38 µm and 32 µm, respectively. The oversize particle weight percentage [%] was calculated for each screen, and the average particle size is expressed as a particle size corresponding to a cumulative weight percentage of 50%.

Apparent Specific Volume

The whole of 10 g of trehalose powder was gently poured into a 100-ml measuring cylinder without making an impact (in this case, a cylinder having an outside diameter smaller than the inside diameter of the measuring cylinder was placed in the measuring cylinder, and it was slowly lifted after pouring the trehalose), and the apparent specific volume was expressed as a value obtained by dividing the read volume by the weight of the trehalose.

Angel of Repose

Measured by means of a Sugiwara's instrument for measuring angle of repose (Yakuzaigaku 27, p. 260, 1965).

Tablet Hardness

About 0.5 g of powder or granules were weighed into a die having a base area of 1 cm$^2$, and held therein under a definite load for 10 seconds to prepare tablets. A load required for breaking the tablet was measured with a Schleuniger hardness meter, and the average of values obtained for 5 tablets was calculated.

Intraoral Disintegration Time

For three healthy male adults subjects, a time required for a molded product to be completely disintegrated by saliva in the mouth was measured. The measurement was carried out twice for each adult and the average of values obtained for the three adults was employed.

Disintegration Time According to Japanese Pharmacopoeia

The disintegration time of each of six molded products was measured by the use of ion-exchanged water according to the disintegration time measuring method prescribed in the 13th revised Japanese Pharmacopoeia, and the average of measured values was calculated.

Whiteness

For powder of trehalose or a pharmaceutical composition containing trehalose, values of L, a and b were measured with a color analyzer (TC-1800MKII, mfd. by Tokyo Denshoku Co., Ltd.), and the whiteness of the trehalose or pharmaceutical composition was calculated by the following equation:

$$\text{Whiteness} = 100 - [(100-L)^2 + (a^2 + b^2)]^{0.5}.$$

Quantitation of Phenylpropanolamine Hydrochloride

A phenylpropanolamine hydrochloride reference standard was dried at 105° C. for 4 hours and about 20 mg of this dried compound was accurately measured. On the other hand, about 1 g of a powder for a paper of the powder was accurately measured. Each of the dried compound and the powder was dissolved in a mobile phase, and then accurately 5 ml of an internal standard solution was added thereto. The total volume of the resulting solution was made to 50 ml by adding the mobile phase. Thus, a standard solution and a sample solution were obtained.

Under the conditions described below, 10 μl of each of the sample solution and the standard solution was tested by liquid chromatography, and the ratio of the peak area of phenylpropanolamine to the peak area of the internal standard substance, $Q_T/Q_S$ was calculated.

Amount (mg) of phenylpropanolamine hydrochloride ($C_9H_{13}NO \cdot HCL$)=amount (mg) of the phenylpropanolamine hydrochloride reference standard×$Q_{T/QS}$.

Operating Conditions

Detector: an ultraviolet spectrophotometer (measuring wavelength: 254 nm).
Column: Octadecyl silica gel was packed in a stainless steel tube having an inside diameter of 4.6 mm and a length of approximately 15 to 30 cm.
Column temperature: 40° C.
Mobile phase: 5 mM sodium hexanesulfonate (adjusted to pH 2.6 with phosphoric acid)/acetonitrile mixed solvent (85/15).
Flow rate: adjusted so that the retention time of phenylpropanolamine might be 5 to 7 minutes.
Internal standard solution:
a solution of methyl p-hydroxybenzoate in the mobile phase (0.02→500).
Yield of Fine Subtilaes
Expressed as the weight percentage of particles which passed through a 355-μm screen and remained on a 75-μm screen, based on the total weight of particles.

EXAMPLE 1

One hundred grams of commercial "Trehaose" (available from Hayashibara Biochemical Laboratories, Inc.) was dissolved in water to a concentration of about 35 wt %, and the resulting solution was concentrated under reduced pressure with heating at 60° C. so as to have a concentration of about 75 wt %, and allowed to stand at room temperature to precipitate crystals, which were washed with 50 ml of water. Glucose was removed by carrying out the above purification procedure once or twice, to increase the trehalose purity. Trehalose A was obtained by carrying out the purification procedure twice to obtain crystals, drying the crystals, grinding the dried crystals with a bantam mill (number of revolutions 15,000 rpm, feed rate 5 kg/hr, and screen opening 2.0 mmφ), and then sifting the ground crystals through a 350-μm screen. Trehalose B was obtained by carrying out the purification procedure once to obtain crystals, drying the crystals, grinding the dried crystals with a bantam mill (number of revolutions 10,000 rpm, feed rate 5 kg/hr, and screen opening 2.00 mmφ), and then sifting the ground crystals through a 350-μm screen. Trehalose C was obtained by carrying out the purification procedure once to obtain crystals, drying the crystals, grinding the dried crystals with a bantam mill (number of revolutions 8,000 rpm, feed rate 5 kg/hr, and screen opening 2.0 mmφ), and then sifting the ground crystals through a 350-μm screen. Trehaloses A to C had the physical properties shown in Table 1. Trehalose A was consolidated during storage as compared with trehaloses B and C. Each of trehaloses A to C was compressed into tablets at a compression pressure of 500 kg/cm², and the tablet hardness immediately after the compression and the tablet hardness after standing for 3 days in an atmosphere of 40° C. and 75% RH after the compression were compared. Table 2 shows the results.

As shown in Table 1, the trehaloses A to C have a good fluidity as indicated by their angle of repose. As shown in Table 2, trehaloses A to C do not change in water content during storage and hence hardly change in tablet hardness because they are dihydrates.

EXAMPLE 2

One gram of each of the trehaloses obtained in Example 1 and 1 g of isoniazid were mixed and then allowed to stand in an atmosphere of 40° C. and 75% RH, and the change in whiteness of the trehalose was observed. On the other hand, 1 g of each of the trehaloses obtained in Example 1 and 1 g of aminophyline were mixed and then allowed to stand in an atmosphere of 40° C. and 75% RH, and the change in whiteness of the trehalose was observed. Table 3 shows the results.

Since the trehaloses A to C had a trehalose purity of 99% or more and a glucose content of less than 1.0% as shown in Table 1, they had a very low reactivity with isoniazid as primary amine, so that their whiteness was maintained at 90% or more with almost no decrease. Similarly, in the case of aminophyline, since the trehaloses A to C had a trehalose purity of 99% or more and a glucose content of less than 1.05, they had a very low reactivity with aminophyline, so that their whiteness was maintained at 90% or more with almost no decrease. However, among trehaloses A to C, trehalose C was decreased in whiteness a little more as compared with trehaloses A and B because it had a trehalose purity of less than 99.3% and a glucose content of more than 0.5%.

Comparative Example 1

One gram of 100-mesh lactose (available from De Melkindustrie Veghel bv) or 1 g of Mannit S (available from Tohwa Kasei Co., Ltd.) and 1 g of aminophyline were mixed and then allowed to stand in an atmosphere of 40° C. and 75% RH, and the change in whiteness of the lactose or Mannit S was observed. Table 4 shows physical properties of the 100-mesh lactose and Mannit S, and Table 5 shows the results of observing the change in whiteness.

The 100-mesh lactose was markedly decreased in whiteness by its reaction with aminophyline. It is known that Mannit S does not react with drugs. The change in whiteness of the trehaloses obtained in Example 1 was equal to that of Mannit S, indicating that the trehaloses have a low reactivity with drugs.

EXAMPLE 3

Four hundreds and ninety grams of each of the trehaloses obtained in Example 1 and 10 g of phenylpropanolamine hydrochloride were mixed in a polyethylene bag and subjected to fluidized-bed granulation (inlet temperature: 75° C., outlet temperature: 29° C., air flow: 20 to 65 m$^3$/hr, and spray rate 21 ml/min) by means of Multiplex (Model MP-01, mfd. by Powrex) to prepare fine subtilaes. Table 6 shows the yield of the fine subtilaes. The fine subtilaes were folded into paper packages in an amount of 1 g per paper package by means of a machine for preparing divided powders, and phenylpropanolamine in each paper package of fine subntilaes was quantitated. For 10 paper packages containing fine subtilaes, the average content of phenylpropanolamine hydrochloride per paper of fine subtilaes and the standard deviation were calculated, and a judgmental value (=|100−average content|+2.2×standard deviation) was calculated according to the method for content uniformity test prescribed in the 13th revised Japanese Pharmacopoeia. Table 6 shows the results.

Since trehaloses A to C had a proportion of particles of 75 $\mu$m or more, an average particle size and an apparent specific volume in the ranges specified in the claim 1 described in the present specification, they had a good miscibility as powder, so that the uniformity of the drug content of the pharmaceutical composition was very good as shown in Table 6. Furthermore, since trehaloses A to C had particle physical properties suitable for granulation, the granulation of only each trehalose and the drug proceeds smoothly, resulting in a very high yield of fine subtilaes.

Comparative Example 2

Trehaloses D and E were prepared by using as a starting material obtained by purifying commercial "Trehaose" (available from Hayashibara Bioscience Laboratories Co., Ltd.) by the method described in Example 1. Trehalose D was obtained by carrying out once the purification procedure described in Example 1 to obtain crystals, drying crystals, grinding the dried crystals with a jet mill (pressure 7.0 kg/cm$^2$, and feed rate 130 kg/hr (maximum screw speed)), and then sifting the ground crystals through a 250-$\mu$m screen. Trehalose E was obtained by carrying out the purification procedure twice to obtain crystals, drying the crystals, grinding the dried crystals with a jet mill (pressure 6.0 kg/cm$^2$, and feed rate 130 kg/hr (maximum screw speed)), and then sifting the ground crystals through a 500-$\mu$m screen. Table 7 shows physical properties of trehaloses D and E.

Since trehalose D has a proportion of particles of 75 $\mu$m or more of less than 2% and an apparent specific volume of more than 3.5 ml/g, its angle of repose is 65°, resulting in a very low fluidity.

Since trehalose E has an apparent specific volume of more than 3.5 ml/g, its angle of repose is more than 50°, resulting in a low fluidity.

EXAMPLE 4

"Trehaose" (available from Hayashibara Bioscience Laboratories Co., Ltd.) was purified once by the method described in Example 1 to obtain crystals, which were dried, ground with a bantam mill (number of revolutions 12,000 rpm, feed rate 5 kg/hr, and screen opening 2.0 mm$\phi$) and then dried at 105° C. for 4 hours to obtain trehalose anhydrous crystals. These crystals were compressed into tablets at a compression pressure of 500 kg/cm$^2$, and the tablet hardnesses of the tablets were compared in the same manner as in Example 1. Tables 8 and 9 show physical properties of the trehalose and the results of the comparison.

Since this trehalose F is in the form of anhydrous crystals as indicated by the melting point shown in Table 8, it adsorbs moisture during the storage of the tablets, resulting in a remarkable decrease in the tablet hardness as shown in Table 9.

EXAMPLE 5

As a starting material. "Trehaose" (available from Hayashibara Bioscience Laboratories Co., Ltd.) was ground with a bantam mill (number of revolutions 15,000 rpm, feed rate 5 kg/hr, and screen opening 2.0 mm$\phi$) without purification and sifted through a 350-$\mu$m screen to obtain trehalose G. The change in whiteness of trehalose G was observed in the same manner as in Example 2. Tables 10 and 11 show physical properties of this trehalose and the observation results.

Since trehalose G was unpurified, it had a high glucose content of 0.9% and its whiteness was decreased to less than 90%.

Comparative Example 3

Trehaloses H and I were prepared by using "Trehaose" (available from Hayashibara Biochemical Laboratories, Inc.) as a starting material. Each of trehalose H and I was obtained by subjecting the starting material twice to the purification procedure described in Example 1 to obtain crystals, drying the crystals, and adjusting the particle size of the dried crystals by the use of a screen without grinding. Four hundreds and ninety grams of each of the trehaloses prepared (whose physical properties are shown in Table 12) and 10 g of phenylpropanolamine hydrochloride were mixed in a polyethylene bag and subjected to fluidized-bed granulation (inlet temperature: 75° C., outlet temperature: 29° C., air flow: 20 to 65 m$^3$/hr, and spray rate: 21 ml/min) by means of Multiplex (Model MP-01, mfd. by Powrex) to prepare fine subtilaes. Separately, 490 g of each of 200-mesh lactose (available from DMV) and Mannit P (available from Tohwa Kasei Co., Ltd.) and 10 g of phenylpropanolamine hydrochloride were mixed in a polyethylene bag and subjected to fluidized-bed granulation (inlet temperature: 75° C., outlet temperature: 29° C., air flow: 20 to 65 m$^3$/hr, and spray rate: 21 ml/min) by means of Multiplex (Model MP-01, mfd. by Powrex) to prepare fine subtilaes. Table 13 shows the yields of the fine subtilaes of the above 4 kinds. The fine subtilaes of each kind were folded in powder papers in an amount of 1 g per paper by means of a machine for preparing divided powders, and phenylpropanolamine in each paper of fine subtilaes was quantitated. For thirty of the paper packages of fine subtilaes, the average content of phenylpropanolamine hydrochloride per paper of fine subtilaes and the standard deviation were calculated, and a judgmental value (=|100−average content|+1.9×standard deviation) was calculated according to the method for content uniformity test prescribed in the 13th revised Japanese Pharmacopoeia. Table 13 shows the results.

Trehalose H had a very good fluidity as indicated by the angle of repose because the proportion of its particles of 75 μm or more is more than 90 wt %. But, as shown in Table 13, the content uniformity in the case of trehalose H was very low because during the mixing, the trehalose H was separated and segregated from the drug having a small average particle size. Moreover, trehalose H had too high a proportion of coarse particles, so that particles formed by the granulation were too large, resulting in a low yield of the fine subtilaes.

Trehalose I had a proportion of particles of 75 μm or more of more than 90 wt %, an average particle size of more than 250 μm and an apparent specific volume of less than 1.5 ml/g, and hence had a very high fluidity as indicated by the angle of repose. But, as shown in Table 13, the content uniformity in the case of trehalose I was very low because during the mixing, trehalose I was separated and segregated from the drug having a small average particle size. Moreover, trehalose I had too high a proportion of coarse particles, so that particles formed by the granulation were too large, resulting in a low yield of the fine subtilaes.

EXAMPLE 6

Trehaloses J and K were prepared by using commercial "Trehaose" (available from Hayashibara Biochemical Laboratories, Inc.) as a starting material. The trehalose J was obtained by subjecting the starting material once to the purification procedure described in Example 1 to obtain crystals, drying the crystals, grinding the dried crystals with a bantam mill (number of revolutions 11,000 rpm, feed rate 5 kg/hr, and screen opening 2.0 mmφ), and sifting the ground crystals through a 350-μm screen. Trehalose K was obtained by subjecting the starting material twice to the purification procedure described in Example 1 to obtain crystals, drying the crystals, grinding the dried crystals with a hantam mill (number of revolutions 12,000 rpm, feed rate 5 kg/hr, and screen opening 2.0 mmφ), and sifting the ground crystals through a 350-μm screen. Table 14 shows physical properties of the trehaloses J and K. Fifty parts by weight of a slightly soluble drug phenacetin (available from Yamamoto Kagaku Kogyo K.K.), 30 parts by weight of each of the trehaloses, 10 parts by weight of corn starch and 10 parts by weight of microcrystalline cellulose (available from Asahi Kasei Kogyo K.K.) were mixed in a polyethylene bag for 3 minutes, and the resulting mixed powder was sprayed with 100 g to 260 g of a 3% hydroxypropyl cellulose (HPC-SL, available from Nippon Soda Co., Ltd.) aqueous solution as a binder solution to obtain granules. Table 15 shows the amount of the binder solution sprayed, the average particle size of the granules, the yield of fine subtilaes, and the tablet hardness of tablets produced by compressing the granules into tablets at a compression pressure of 1,000 kg/cm$^2$. Trehaloses J and K had a proportion of particles of 75 μm or more, an average particle size and an apparent specific volume in the ranges specified in the present invention, and hence had an excellent suitability for granulation. When each of trehaloses J and K was used as an excipient, sufficient granulation proceeds even when the amount of the binder solution was small. Furthermore, the yield of fine granules was high and granules of a uniform size could be obtained. In addition, when the amount of the binder solution was controlled, the granule hardness became 4.5 kg or more, indicating that trehaloses J and K are excellent also in compactibility.

Comparative Example 4

Granules were prepared by using each of the trehalose D prepared in Comparative Example 2,200-mesh lactose and Mannit P in place of the trehalose obtained in Example 6. In detail, 50 parts by weight of a slightly soluble drug phenacetin (available from Yamamoto Kagaku Kogyo K.K.), 30 parts by weight of each of the trehalose D, 200-mesh lactose and Mannit P, 10 parts by weight of corn starch and 10 parts by weight of microcrystalline cellulose (available from Asahi Kasei Kogyo K.K.) were mixed in a polyethylene bag for 3 minutes, and the resulting mixed powder was sprayed with 100 g to 260 g of a 3% hydroxypropyl cellulose (HPC-SL, available from Nippon Soda Co., Ltd.) aqueous solution as a binder solution to obtain granules. Table 16 shows the amount of the binder solution sprayed, the average particle size of the granules, the yield of fine subtilaes and the tablet hardness of tablets produced by compressing the granules into tablets at a compression pressure of 1,000 kg/cm$^2$.

Trehalose D contained such a large amount of fine particles that the proportion of particles of 75 μm or more was less than 2 wt %, and hence its apparent specific volume was more than 3.5 cm$^3$/g. Therefore, when trehalose D was used, a large amount of the binder solution was required for obtaining the same particle size as in the case of the trehalose obtained in Example 6, so that the granulation time and the drying time were elongated. Accordingly, trehalose D was judged as undesirable. In the case of trehalose D, the tablet hardness was good, but the yield of fine subtilaes was low and granules having a wide particle size distribution were obtained, namely, the granulating properties were deteriorated.

As compared with trehalose D, the 200-mesh lactose and Mannit P had lower granulating properties, and required a larger volume of the binder solution and elongated granulation time and drying time. Therefore, it was judged that they raise the cost of preparation of wet granules. Moreover, they imparted only a low tablet hardness, namely, they were poor in compactibility. They were inferior to the trehalose of the present invention also in the yield of fine subtilaes.

EXAMPLE 7

The wet granules obtained in Example 6 were subjected to a dissolution test according to the dissolution test prescribed in the 13th revised Japanese Pharmacopoeia. The first liquid listed in the Japanese Pharmacopoeia was used as a test liquid, and the drug dissolution rate after 5 minutes was measured. The dissolution rate was calculated by taking the total amount of the drug contained in the granules as 100%. Table 17 shows the results. In the case of the trehaloses J and K, the dissolution rate after 5 minutes was as very high as 80%.

Comparative Example 5

The granules prepared from each of lactose and Mannit P in Comparative Example 4 were subjected to a dissolution test according to the dissolution test prescribed in the 13th revised Japanese Pharmacopoeia. The first liquid listed in the Japanese Pharmacopoeia was used as a test liquid, and the drug dissolution rate after 5 minutes was measured. The drug dissolution rate was calculated by taking the total amount of the drug contained in the granules as 100%. Table 17 shows the results. In the case of lactose and Mannit P, the dissolution rate after 5 minutes was lower than in the case of trehaloses J and K.

EXAMPLE 8

One kilogram of each of the trehaloses obtained in Example 1 was charged into a planetary mixer (mfd. by Shinagawa Seisakusho Co., Ltd.), sprayed with 80 g of water with stirring, and then granulated. 0.5 Gram of the resulting granules were molded into a column with a diameter of 11 mm at a pressure of 30 kg/cm$^2$. The column was dried overnight at 40° C. to obtain a rapidly disintegrable molded product. Table 19 shows the hardness and disintegration time of the molded product.

EXAMPLE 9

Nine hundreds and fifty grams of each of trehaloses A, B and C obtained in Example 1 and 50 g of phenylpropanolamine hydrochloride were charged into a planetary mixer, sprayed with 80 g of water with stirring, and then granulated. The resulting granules (0.5 g) were molded into a column with a diameter of 11 mm at a pressure of 30 kg/cm$^2$. The column was dried overnight at 40° C. to obtain a rapidly disintegrable molded product. Table 19 shows the hardness and disintegration time of the molded products thus obtained.

EXAMPLE 10

Rapidly disintegrable molded products were obtained by repeating the process of Example 9 except for conducting the molding at a pressure of 60 kg/cm$^2$. Table 19 shows the hardness and disintegration time of the molded products.

EXAMPLE 11

Seven hundreds and fifty grams of the trehalose B obtained in Example 1, 200 g of corn starch and 50 g of phenylpropanolamine hydrochloride were charged into a planetary mixer, sprayed with 150 g of water with stirring, and then granulated. The resulting granules (0.5 g) were molded into a column with a diameter of 11 mm at a pressure of 60 kg/cm$^2$. The column was dried overnight at 40° C. to obtain a rapidly disintegrable molded product. Table 19 shows the hardness and disintegration time of the molded product.

Comparative Example 6

A molded product was obtained by repeating the process of Example 9 except for using commercial "Mannitol P" (available from Towa Kasei Co., Ltd.). Table 19 shows the results.

Comparative Example 7

A molded product was obtained by repeating the process of Example 9 except for using the trehalose I obtained in Comparative Example 3. Table 19 shows the hardness and disintegration time of the molded product. The molded product felt rough in mouth, namely, it gave an unpleasant feeling when taken.

Comparative Example 8

As a starting material, "Trehaose" was ground with a bantam mill (number of revolutions, 12,000 rpm, feed rate 5 kg/hr, and screen opening 2.0 mmφ) and sifted through a 350-μm screen to obtain trehalose L. Table 18 shows physical properties of the trehalose L.

A molded product was obtained by repeating the process of Example 9 except for using the trehalose L. Table 19 shows the hardness and disintegration time of the molded product.

This molded product and the rapidly disintegrable molded product obtained in Example 9 by using the trehalose B were placed in separate glass bottles, respectively, and stored at 40° C. for 3 months. As a result, the former was not changed in color, while the latter was somewhat yellowed.

Comparative Example 9

Trehalose M was obtained by carrying out once the purification procedure described in Example 1 to obtain crystals, drying the crystals and then violently grinding the dried crystals with a bantam mill (number of revolutions 18,000 rpm, feed rate 1 kg/hr, and screen opening 0.5 mmφ). Table 18 shows physical properties of trehalose M.

Although trehalose M had remarkable aggregating properties and hence made it difficult to disperse the components of a molded product, the molded product was produced by repeating the process of Example 9 except for using trehalose M and changing the amount of water added to 150 g. Table 19 shows the hardness and disintegration time of the molded product.

EXAMPLE 12

Nine hundreds and fifty grams of the trehalose A obtained in Example 1 and 50 g of ascorbic acid were charged into a planetary mixer, sprayed with 100 g of water with stirring, and then well kneaded. The kneaded product was sifted through a screen having an opening of 840 μm, and particles passed through the screen were dried overnight at 40° C. Table 20 shows physical properties of tablets obtained by compressing the dried particles at a compression pressure of 500 or 800 kg/cm$^2$. Separately, tablets were produced by the same procedure as above except for using as a starting material a mixture obtained by mixing 750 g of the trehalose A obtained in Example 1,200 g of microcrystalline cellulose ("Avicel" PH-101, mfd. by Asahi Kasei Kogyo K.K.) and 50 g of ascorbic acid in a polyethylene bag for 3 minutes. Table 20 shows physical properties of these tablets.

Comparative Example 10

A starch partial-degradation product (Pinedex #4, available from Matsutani Chemical Industry Co., Ltd.) was treated with a non-reducing sugar producing enzyme, and then the enzyme was inactivated. The reaction solution was desalted by the use of an ion-exchange resin without decoloring with activated carbon, and then concentrated so as to have a concentration of 60%. The concentrate was subjected to a column chromatography by the use of a salt type strongly acidic cation-exchange resin to obtain a fraction having a high trehalose content, which was concentrated, followed by two repetitions of recrystallization, whereby trehalose crystals were obtained. The trehalose crystals were ground with a bantam mill (number of revolutions 10,000 rpm, feed rate 5 kg/hr, and screen opening 2.0 mmφ) to obtain trehalose N. As shown in Table 21, trehalose N had such a low whiteness that it had no attractive appearance.

Industrial Applicability

According to the present invention, an excipient comprising trehalose can be provided which has a low reactivity and imparts various physical properties required for preparing a pharmaceutical composition, such as fluidity, miscibility (content uniformity), granulating properties, hygroscopicity, compactibility, disintegrating properties (solubility) and the like with good balance among them. The excipient of the present invention has the above-mentioned various physical properties at the same time and hence can give a pharmaceutical composition having desirable physical properties, even when used alone without combination with other excipients. In addition, since the rapidly disintegrable molded product of the present invention has very excellent disintegrating properties, it is easy to take and it gives a good feeling when taken. At the same time, the molded product is good in hardness and hence is good in stability during transportation and storage. Furthermore, the trehalose is advantageous in that it has little laxative effect and a proper sweetness.

TABLE 1

| Trehalose | Melting point (° C.) | Trehalose purity (%) | Glucose content (%) | Proportion of particles of 75 μm or more (%) | Average particle size (μm) | Apparent specific volume (cm$^3$/g) | Whiteness (%) | Angle of repose (°) |
|---|---|---|---|---|---|---|---|---|
| A | 97 | 99.5 | 0.2 | 15 | 35 | 3.1 | 98 | 48 |
| B | 97 | 99.3 | 0.3 | 46 | 72 | 2.2 | 97 | 42 |
| C | 97 | 99.2 | 0.6 | 73 | 127 | 1.9 | 95 | 40 |

TABLE 2

| | 0 day | | 3 days | |
|---|---|---|---|---|
| Trehalose | Water content | Tablet hardness (kgf) | Water content | Tablet hardness (kgf) |
| A | 9.7 | 2.6 | 9.8 | 2.5 |
| B | 9.8 | 2.5 | 9.8 | 2.4 |
| C | 9.8 | 2.3 | 9.8 | 2.3 |

TABLE 3

| | | Whiteness (%) | |
|---|---|---|---|
| Drug | Trehalose | 0 day | 1 month |
| Isoniazid | A | 98 | 97 |
| | B | 98 | 96 |
| | C | 97 | 93 |
| Aminophyline | A | 100 | 98 |
| | B | 99 | 97 |
| | C | 98 | 93 |

TABLE 4

| Excipient | Proportion of particles of 75 μm or more (%) | Average particle size (μm) | Apparent specific volume (cm$^3$/g) | Angle of repose (°) |
|---|---|---|---|---|
| 100-Mesh lactose | 76 | 104 | 1.5 | 43 |
| Mannit 5 | 68 | 102 | 1.7 | 53 |

TABLE 5

| | Whiteness (%) | | |
|---|---|---|---|
| Excipient | 0 day | 5 days | 1 month |
| 100-Mesh lactose | 99 | 30 | — |
| Mannit S | 100 | 98 | 93 |

TABLE 6

| Trehalose | Yield of fine granules (%) | Average content per paper (%) | Standard deviation | Judgmental value |
|---|---|---|---|---|
| A | 95 | 97 | 0.31 | 3.7 |
| B | 94 | 98 | 1.03 | 4.3 |
| C | 93 | 98 | 1.04 | 4.3 |

TABLE 7

| Trehalose | Melting point (° C.) | Trehalose purity (%) | Glucose content (%) | Proportion of particles of 75 μm or more (%) | Average particle size (μm) | Apparent specific volume (cm³/g) | Whiteness (%) | Angle of repose (°) |
|---|---|---|---|---|---|---|---|---|
| D | 97 | 99.0 | 0.4 | 1 | 12 | 4.5 | 96 | 65 |
| E | 97 | 99.3 | 0.2 | 3 | 25 | 3.7 | 96 | 55 |

TABLE 8

| Trehalose | Melting point (° C.) | Trehalose purity (%) | Glucose content (%) | Proportion of particles of 75 μm or more (%) | Average particle size (μm) | Apparent specific volume (cm³/g) | Whiteness (%) | Angle of repose (°) |
|---|---|---|---|---|---|---|---|---|
| F | 203 | 99.0 | 0.4 | 28 | 49 | 2.3 | 94 | 45 |

TABLE 9

| | 0 day | | 3 days | |
|---|---|---|---|---|
| Trehalose | Water content | Tablet hardness (kgf) | Water content | Tablet hardness (kgf) |
| F | 0.5 | 4.5 | 9.8 | 2/4 |

TABLE 10

| Trehalose | Melting point (° C.) | Trehalose purity (%) | Glucose content (%) | Proportion of particles of 75 μm or more (%) | Average particle size (μm) | Apparent specific volume (cm³/g) | Whiteness (%) | Angle of repose (°) |
|---|---|---|---|---|---|---|---|---|
| G | 97 | 99.0 | 0.9 | 13 | 31 | 3.1 | 94 | 49 |

TABLE 11

| | Whiteness (%) | |
|---|---|---|
| Trehalose | 0 day | 1 month |
| G | 94 | 87 |

TABLE 12

| Trehalose | Melting point (° C.) | Trehalose purity (%) | Glucose content (%) | Proportion of particles of 75 μm or more (%) | Average particle size (μm) | Apparent specific volume (cm³/g) | Whiteness (%) | Angle of repose (°) |
|---|---|---|---|---|---|---|---|---|
| Trehalose H | 97 | 99.2 | 0.3 | 91 | 180 | 1.5 | 98 | 37 |
| Trehalose I | 97 | 99.4 | 0.2 | 95 | 280 | 1.4 | 96 | 30 |
| 200M lactose | — | — | — | 15 | 60 | 2.1 | 95 | 45 |
| Mannit P | — | — | — | 20 | 47 | 2.1 | 96 | 45 |

TABLE 13

| Excipient | Yield of fine subtilaes (%) | Average content per paper (%) | Standard deviation | Judgmental value |
|---|---|---|---|---|
| Trehalose H | 50 | 98 | 15.4 | 35.9 |
| Trehalose I | 40 | 97 | 16.0 | 33.4 |
| 200 M lactose | 75 | 97 | 11.2 | 24.3 |
| Mannit P | 85 | 98 | 6.1 | 13.6 |

TABLE 14

| Trehalose | Melting point (° C.) | Trehalose purity (%) | Glucose content (%) | Proportion of particles of 75 μm or more (%) | Average particle size (μm) | Apparent specific volume (cm³/g) | Whiteness (%) | Angle of repose (°) |
|---|---|---|---|---|---|---|---|---|
| J | 97 | 99.4 | 0.5 | 40 | 60 | 2.0 | 96 | 41 |
| K | 97 | 99.6 | 0.1 | 21 | 50 | 2.1 | 97 | 42 |

TABLE 15

| Trehalose | Amount of binding solution (g) | Average particle size of granules (μm) | Yield of fine granules (%) | Tablet hardness at a compression pressure of 1000 kg/cm² (kgf) |
|---|---|---|---|---|
| J | 100 | 110 | 70 | 5.1 |
|   | 120 | 130 | 85 | 4.7 |
|   | 160 | 270 | 80 | 3.0 |
| K | 100 | 120 | 74 | 5.0 |
|   | 120 | 140 | 85 | 4.5 |
|   | 160 | 180 | 80 | 2.9 |

TABLE 16

| Excipient | Amount of binding solution (g) | Average particle size of granules (μm) | Yield of fine granules (%) | Tablet hardness at a compression pressure of 1000 kg/cm² (kgf) |
|---|---|---|---|---|
| Trehalose D | 100 | 80 | 55 | 4.5 |
|   | 120 | 121 | 48 | 4.1 |
|   | 160 | 205 | 37 | 3.0 |
| 200 M lactose | 180 | 91 | 70 | 2.5 |
|   | 220 | 150 | 75 | 3.0 |
|   | 240 | 220 | 75 | 3.7 |
| Mannit P | 180 | 106 | 80 | 3.9 |
|   | 200 | 144 | 80 | 3.0 |
|   | 240 | 313 | 35 | 3.1 |

TABLE 17

|  | Excipient | Binding solution | Average particle size of granules (μm) | Drug dissolution rate after 5 min. (%) |
|---|---|---|---|---|
| Example 7 | Trehalose J | 120 | 130 | 80 |
|  | Trehalose K | 160 | 180 | 80 |
| Comparative | Lactose | 240 | 220 | 60 |
| Example 5 | Mannit P | 200 | 144 | 70 |

TABLE 18

| Trehalose | Trehalose purity (%) | Glucose content (%) | Proportion of particles of 75 μm or more (%) | Average particle size (μm) | Apparent specific volume (ml/g) | Whiteness (%) |
|---|---|---|---|---|---|---|
| L | 98.7 | 1.0 | 25 | 45 | 2.5 | 95 |
| M | 99.2 | 0.3 | 1 | 8 | 3.8 | 97 |

TABLE 19

|  |  | Tablet hardness (kg) | Intraoral disintegration time (sec) | Digestion time according to Japanese pharmacopoeia (sec) |
|---|---|---|---|---|
| Example 8 | A | 7.5 | 18 | 15 |
|  | B | 6.6 | 18 | 12 |
|  | C | 6.0 | 14 | 10 |
| Example 9 | A | 7.0 | 16 | 16 |
|  | B | 6.5 | 18 | 14 |
|  | C | 5.6 | 15 | 10 |
| Example 10 | A | 10.2 | 60 | 52 |
|  | B | 9.4 | 56 | 45 |
|  | C | 8.6 | 42 | 33 |
| Example 11 |  | 7.2 | 26 | 18 |
| Comparative Example 6 |  | 0.8 | 20 | 15 |
| Comparative Example 7 |  | 3.5 | 30 | 23 |
| Comparative Example 8 |  | 6.7 | 18 | 15 |
| Comparative Example 9 |  | 7.2 | 130 | 140 |

TABLE 20

| Excipient | Compression pressure (kg/cm$^2$) | Tablet hardness (kgf) | Disintegration time according to Japanese Pharmacopoeia (sec) |
|---|---|---|---|
| Trehalose A | 500 | 4.0 | 17 |
|  | 800 | 7.0 | 25 |
| Trehalose A + microcrystalline cellulose | 300 | 4.0 | 15 |
|  | 500 | 6.5 | 23 |

TABLE 21

| Trehalose | Trehalose purity (%) | Glucose content (%) | Proportion of particles of 75 μm or more (%) | Average particle size (μm) | Apparent specific volume (ml/g) | Whiteness (%) |
|---|---|---|---|---|---|---|
| N | 99.2 | 0.4 | 45 | 70 | 2.2 | 88 |

What is claimed is:

1. An excipient comprising α,α-trehalose dehydrate obtained in a crystal form by treating, with enzymes, a starch degradation product(s) with the degree of polymerization of 3 or more, wherein the α,α-trehalose dehydrate has a purity of 99.0% or more, a glucose content of 0.5% or less, a water content of 12.0% or less, a proportion of particles of 75 μm or more of 2 to 90 wt %, an average particle size of 10 to 250 μm, an apparent specific volume of 1.5 to 3.5 ml/g, and a whiteness of 96% or more.

2. The excipient according to claim 1, wherein α,α-trehalose dehydrate has the purity of 99.3% or more, and the average particle size of 10 to 150 μm.

3. The excipient according to claim 2, which has an average particle size of 30 to 150 μm.

4. A process for formulating a solid form comprising:
combining a drug and the excipient of claim 1.

5. A pharmaceutical composition comprising a drug and the excipient according to any one of claims 1, 2, and 3.

6. The pharmaceutical composition according to claim 5, which is a rapidly disintegrable molded product.

7. The pharmaceutical composition according to claim 6, which further comprises a cellulose.

8. A process for producing the excipient according to any one of claims 1, 2, and 3, comprising:
processing the trehalose crystals by at least one treating method selected from the group consisting of purification, grinding, sieving and re-crystallization.

9. The process of claim 8, wherein the trehalose crystals are ground to be subsequently sieved.

10. The process according to claim 9, wherein the trehalose crystals are ground with a small amount of impact energy.

* * * * *